(12) United States Patent  
Masseglia et al.

(10) Patent No.: US 8,070,689 B2
(45) Date of Patent: Dec. 6, 2011

(54) PERFORATING TROCAR

(75) Inventors: Thierry Masseglia, La Farlède (FR); Laurent Fumex, St Arnoult en Yvelines (FR)

(73) Assignee: Laurane Medical, St. Arnoult en Yvelines (FR)

( * ) Notice: Subject to any disclaimer, the term of this patent is extended or adjusted under 35 U.S.C. 154(b) by 0 days.

(21) Appl. No.: 11/808,400

(22) Filed: Jun. 8, 2007

(65) Prior Publication Data

US 2008/0306405 A1 Dec. 11, 2008

(51) Int. Cl.
*A61B 10/00* (2006.01)
*A61B 17/32* (2006.01)

(52) U.S. Cl. ........................ 600/567; 600/170

(58) Field of Classification Search .................. 600/562, 600/564, 567, 568; 606/79, 80, 81, 167, 606/170

See application file for complete search history.

(56) References Cited

U.S. PATENT DOCUMENTS

| 5,330,972 | A | * | 7/1994 | Cope .................................. 514/2 |
| 5,697,935 | A | * | 12/1997 | Moran et al. ................... 606/104 |
| 5,810,826 | A | * | 9/1998 | Åkerfeldt et al. ............... 606/80 |
| 6,312,432 | B1 | * | 11/2001 | Leppelmeier .................... 606/80 |
| 2003/0199879 | A1 | * | 10/2003 | Spranza, III .................... 606/79 |
| 2004/0215102 | A1 | * | 10/2004 | Ikehara et al. ................. 600/562 |

FOREIGN PATENT DOCUMENTS

GB 2164277 A * 3/1986

* cited by examiner

*Primary Examiner* — Max Hindenburg
*Assistant Examiner* — Jonathan M Foreman
(74) *Attorney, Agent, or Firm* — Merchant & Gould

(57) ABSTRACT

The invention concerns the field of surgical instruments. The inventive trocar (1) is of the type comprising a rigid tube (2) wherein may slide a rod (3) with a perforating distal tip, and it is characterized in the distal tip zone of the rod forms a perforating drill capable of rotating on its axis while the distal end of the tube is divided into at least two segments (10, 11), with helical cutting edge. The invention is applicable in particular to bone biopsy.

9 Claims, 3 Drawing Sheets

PERFORATING TROCAR

The present invention relates to the field of instruments that can be used in surgery and in interventional radiology, and more particularly to a perforating trocar that can be used especially in the field of bone biopsy, cementoplasty of the skeletal areas, and treatment of bone damage by photocoagulation or thermocoagulation.

BACKGROUND OF THE INVENTION

Various types of trocars are known that are surgical instruments used to gain access to natural or pathological cavities, to carry out biopsies or to introduce substances, for example to perform intestinal or gynecological celioscopy, or to perform endoscopic operations, in particular arthroscopic operations, by which it is possible to greatly reduce the patient's post-operative recovery period by comparison with procedures involving open surgery. A trocar is generally composed of a hollow tube, also called a cannula or sheath, in which a rod or obturator is able to slide, the distal end of which rod or obturator emerges at the distal end of the tube and is in the form of a tip in order to facilitate penetration into the tissues.

Thus, the patent FR 2,697,150 describes a trocar intended for celioscopy and comprising a tube in which a hollow rod engages which is provided with a tip having recessed facets and capable of containing a device for protecting the tip. The patent application WO 03020140 describes a trocar designed to require only minimal force for insertion into the tissues, so as to reduce as far as possible the damage caused by the penetration, said trocar comprising a tip at the distal end of the obturator, fitting perfectly in the continuation of the distal opening of the cannula, which has a certain degree of flexibility. Such a trocar is intended essentially to be introduced into the soft tissues. Another type of trocar is described in the patent application WO 03045260, according to which a perforating obturator is able to slide in the cannula of the trocar in order to pierce the abdominal wall of a patient during a laparoscopy operation involving introduction of a gas into the abdominal cavity in order to distend it and make the operation easier. However, the trocar according to said document is not designed to perforate a hard wall, such as that of a bone.

Some types of perforating trocars are also known, and are available on the surgical instruments market, which comprise a tip associated with a tube with a cutting distal edge in order to permit penetration into a relatively hard bone, but the effectiveness of trocars of this type is not always satisfactory, particularly in the case of very hard bone resisting conventional cutting tools. Thus, the patent U.S. Pat. No. 5,810,826 describes a perforating trocar comprising a rod with an end in the form of a drill-bit with eccentric tip, guided by a tube. When the rod comes into contact with the bone, its rotation causes the formation of a hole with a diameter wider than that of the rod, by virtue of the off-centered position of the tip, while the tube is held immobile. The use of this trocar is difficult because the operator has to hold the tube with one hand and turn the rod with the other hand.

SUMMARY OF THE INVENTION

The subject matter of the present invention is a perforating trocar that permits a very effective perforation and that is very easy to use and safe to handle.

The invention also relates to a perforating trocar with which it is possible, under good conditions of efficacy and reliability, to perform operations such as bone biopsies, vertebroplasty procedures, and treatment of lesions.

The trocar according to the present invention is of the type comprising a rigid tube in which a rod with a perforating distal tip is able to slide, and it is characterized in that the zone of the distal tip of the rod has the form of a perforating drill-bit that is able to turn on its axis, while the distal end of the tube is divided into at least two segments with a helical cutting edge. According to the invention, each helical segment corresponds to an angle of less than or equal to 180° about the axis of the tube.

The segments with a helical cutting edge are preferably identical or have like or similar profiles. Segments with like profiles means segments that are substantially identical or that differ only in minor details. Segments with similar profiles means segments that are the same shape but have different dimensions.

BRIEF DESCRIPTON OF THE DRAWINGS

DETAILED DESCRIPTION OF THE PREFERRED EMBODIMENTS

Figure 1:
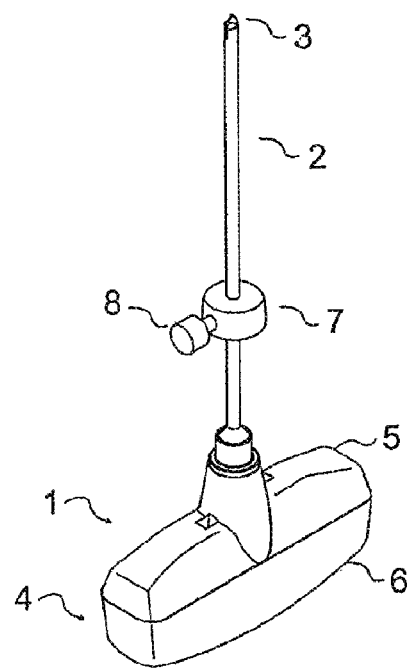
FIG. 1 shows an overall view of a trocar according to the present invention.

According to an advantageous embodiment of the invention, the distal end of the tube is divided into two symmetrical segments along the axis of the tube, and the cutting edge of each part forms a helical ramp inclined by 1 to 45°, preferably by 10 to 30°, with respect to the plane perpendicular to the axis. The edges of these parts, depending on the thickness of the tube, can be sharpened to improve the efficacy of the cut, for example by providing a beveled section.

According to a preferred embodiment, the helical edge parts of the distal end of the tube are separated by a recess cut out in the wall of the tube, the depth of the recess, from the lower edge of the helical ramp to the bottom of the recess, being between 0.5 and 5 times, preferably between 1 and 2 times, the internal diameter of the tube.

According to another feature of the invention, the zone of the distal tip of the rod comprises at least two cutting ridges that extend from a point situated preferably on the axis to the periphery of the tip. According to a preferred embodiment, these cutting ridges are arranged symmetrically with respect to the axis of the rod, and their profiles can be identical to or different than one another. For example, two cutting ridges can be arranged on either side of the axis of the rod and off-centered relative to the latter. In a variant according to the invention, the cutting ridges extend from a point that is slightly off-centered relative to the axis.

According to an advantageous embodiment of the invention, at least part of the body of the rod has the form of a perforating drill-bit with two helical flutes. The attacking surfaces of the distal tip are delimited by the cutting ridges and have a concave shape joining each flute, thus facilitating the perforation of a hard surface, for example that of a bone, when the rod is applied against such a surface and a movement of rotation is applied to it.

The above-described rod with a tip in the form of a drill-bit can be withdrawn from the tube after perforation of the bone, in order to be replaced, for example, by a biopsy needle or cannula or by an ultrasound probe or fiber optics.

The trocar of the invention can thus be used not only in bone biopsy, but also in cementoplasty for the skeletal areas, in particular in vertebroplasty for injection of a bone-filling cement, or for treatment of damaged bone by photocoagulation with the aid of a fiber-optic laser, or by thermocoagulation with the aid of a radio-frequency or ultrasound apparatus.

By way of example, in the case where a biopsy of damaged bone behind a hard bone is to be carried out, the practitioner, having induced local anesthesia by conventional techniques, introduces the trocar, comprising the tube and a rod with a pointed distal end, through the skin and the soft tissues of the patient until it contacts the bone. A control abutment, which is movable on the tube of the trocar, ensures that the depth of insertion is controlled as a function of the distance by which the bone is to be perforated. The rod is then withdrawn, leaving the tube in place, its distal end being against the wall of the bone. The perforating rod is then inserted into the sheath until its handle is locked, its tip then being in contact with the bone, and the assembly made up of the tube and of the perforating rod is then subjected to a rotation movement in order to drill the bone. The biopsy is then performed by replacing the perforating rod by a suitable instrument, for example a biopsy needle.

The structure of the trocar according to the invention has the advantage of making it very easy to use, since it can be put in place and maneuvered with just one hand by virtue of the cooperation between the sheath with cutting edges and the rod with perforating tip, which are integral during the movement of perforation by rotation.

The simplicity of the structure of the trocar according to the invention makes it possible to provide the user with an assembly or kit composed of several trocars, tubes, solid rods or hollow rods, and perforating or extracting needles, this assembly being adapted to use in surgery, and more particularly to the conduct of bone biopsies, for example for fairly deep lesions.

Other features and advantages of the present invention will become clear from the following description of a preferred embodiment, with reference being made to the attached drawings, in which:

FIG. 1 shows an overall view of a trocar according to the present invention.

Figure 2:
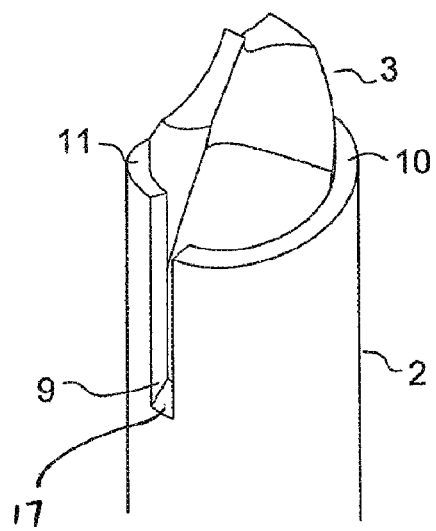
FIG. 2 shows a perspective view of the tip of the trocar from FIG. 1, illustrating the distal ends of the tube and of the inner rod.

FIG. 2 shows a perspective view of the tip of the trocar from FIG. 1, illustrating the distal ends of the tube and of the inner rod.

Figure 3:
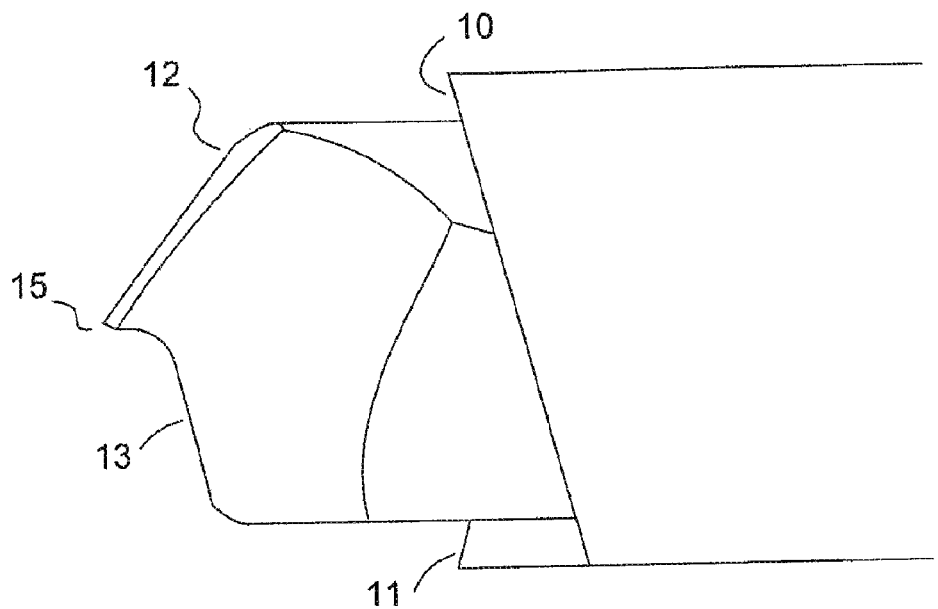
FIG. 3 shows a plan view of the tip of the trocar, illustrating the respective positions of the tube and of the rod.

FIG. 3 shows a plan view of the tip of the trocar, illustrating the respective positions of the tube and of the rod.

Figure 4:
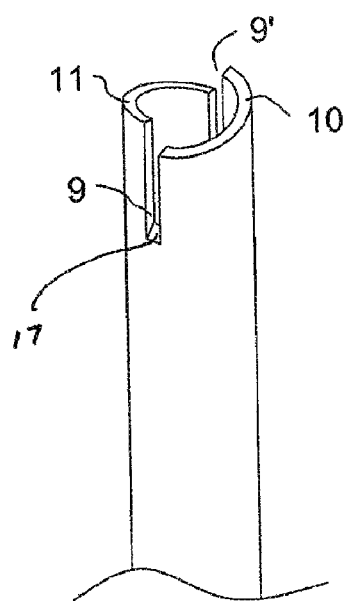
FIG. 4 shows a view of the distal end of the tube alone, without the rod.

FIG. 4 shows a view of the distal end of the tube alone, without the rod.

Figure 5:
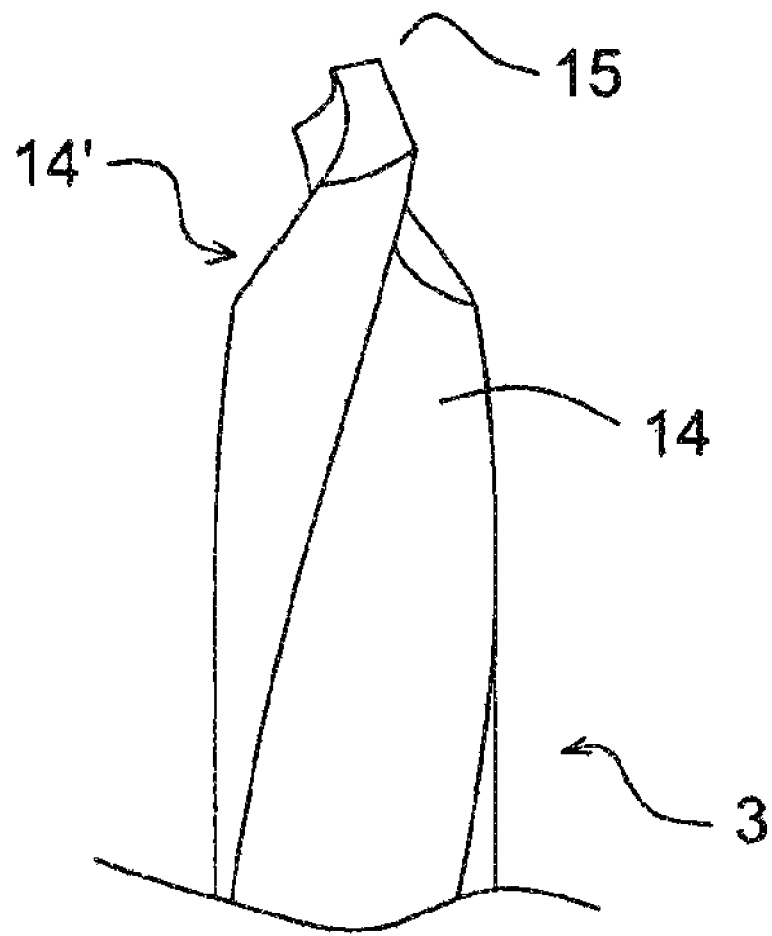
FIG. 5 shows a view of the distal end of the rod alone, without the tube.

FIG. 5 shows a view of the distal end of the rod alone, without the tube.

The trocar (1) shown in FIG. 1 comprises a hollow cylindrical tube (2) in which a rod (3) is able to slide and pivot. The trocar (1) also comprises a handle (4), which allows it to be maneuvered by the user and which comprises two parts, namely an inner part (5) integral with the tube (2), and an outer part (6) integral with the rod (3). The two parts (5 and 6) of the handle (4) can be displaced relative to each other in order to move the rod (3) in the tube (2) of the trocar, either in a sliding movement by pulling the part (6) of the handle away from the part (5), or in a pivoting movement by turning the part (6) with respect to the part (5) of the handle.

The trocar (1) also comprises an abutment (7) whose position on the tube (2), can be adjusted by way of a screw (8).

As is shown in FIG. 2, which depicts the tip of the trocar in detail, the tube (2) has two recesses of rectangular cross section, of which only one (9) is visible in FIG. 2. These two recesses (9) and (9') divide the end of the tube (2) into two lips (10) and (11), which have a helical cutting ridge and which are arranged symmetrically with respect to the axis of the tube, as is shown more clearly in FIG. 4. These two recesses (9) and (9') each have a base 17 inclined downward and outwardly to facilitate the evacuation of bone debris.

The distal end of the rod (3) has the form of a perforating drill-bit, which is shown better in FIG. 5 and which emerges beyond the end of the tube when it is inserted fully in the tube (2), in such a way that the two parts (5) and (6) of the handle (4) are then joined, in the position shown in FIG. 1.

The elevation view in FIG. 3 shows the tip of the trocar (1), the respective positions of the two lips (10) and (11) that are symmetrical with respect to the axis, and the two cutting ridges (12) and (13) whose profiles differ from one another. The inclination of the cutting ridge of the lips with respect to the plane perpendicular to the axis of the rod is approximately 15°.

The two recesses (9) and (9') appearing in FIG. 4 have a base 17 inclined downward and outwardly to facilitate the evacuation of the bone debris during perforation by means of the cutting lips (10) and (11), the action of which combines with that of the tip of the rod (3) when the user pivots it on its axis in the tube (2).

As is shown in FIG. 5, the tip of the rod (3) has the form of a perforating drill-bit with two helical flutes (14) and (14') and a terminal end forming a cutting ridge (15) substantially on the axis of the rod (3), in such a way that the rotation of the rod in the reverse direction (direction of the hands of a clock), when the tip of the rod (3) is against a bone wall, promotes the perforation of said bone wall. The attacking surfaces of the cutting ridges (12) and (13) have a concave shape delimited on one side by the cutting ridges (12) and (13) and on the other sides by the end of the helical flutes (14) and (14').

The invention claimed is:

1. Perforating trocar comprising a rigid tube in which a rod with a perforating distal tip is able to slide, wherein the zone of the distal tip of the rod has the form of a perforating drill-bit that is able to turn on its axis, while the distal end of the tube includes recesses dividing the distal end into at least two segments with a helical cutting edge; with each recess having an axial outer end which intersects the distal end of the tube at axially spaced locations, and with each of said helical cutting edges extending helically from said axial outer end of one of said recesses to said axial outer end of another of said recesses, wherein the segments with a helical cutting edge of the distal end of the tube are separated by said recesses, which are cut through the wall of the tube, and with the base of each of the recesses inclined downward and outwardly to facilitate the evacuation of bone debris.

2. Perforating trocar according to claim 1, wherein each segment with a helical cutting edge corresponds to an angle of less than or equal to 180° about the axis of the tube.

3. Perforating trocar according to claim 2, wherein the distal end of the tube is divided into two symmetrical segments along the axis of the tube.

4. Trocar according to claim 1, wherein the cutting edge of each of the at least two segments forms a helical ramp inclined by 10 to 30° with respect to the plane perpendicular to the axis.

5. Trocar according to claim 1, wherein the depth of the recess, from the lower edge of a helical ramp formed from the cutting edge of each segment to the bottom of the recess, is between 0.5 and 5 times the internal diameter of the tube.

6. Trocar according to claim 1, wherein the zone of the distal tip of the rod comprises at least two cutting ridges that extend from a point situated on the axis to the periphery of the tip.

7. Trocar according to claim 6, wherein the zone of the distal tip of the rod comprises two cutting ridges that are arranged on either side of the axis of the rod and are off-centered relative to the latter.

8. Trocar according to claim 1, wherein the distal zone of the rod has the form of a perforating drill-bit with two helical flutes, and the attacking surfaces of the distal tip, which are delimited by cutting ridges, have a concave shape joining each flute.

9. Trocar according to claim 1, wherein the rod is capable of sliding longitudinally or pivot.

* * * * *